United States Patent [19]

Moden et al.

[11] Patent Number: 4,941,472
[45] Date of Patent: Jul. 17, 1990

[54] ELECTRICAL ACCESS PORT ASSEMBLY

[75] Inventors: James R. Moden, Bristol; Michael D. Caldwell, East Greenwich; Robert D. Moden, Warren, all of R.I.

[73] Assignee: Surgical Engineering Associates, Inc., Bristol, R.I.

[21] Appl. No.: 338,232

[22] Filed: Apr. 13, 1989

[51] Int. Cl.$^5$ .............................................. A61N 1/00
[52] U.S. Cl. .............................................. 128/419 PS
[58] Field of Search ................. 128/419 PS, 785, 786, 128/734

[56] References Cited

U.S. PATENT DOCUMENTS 4,804,054 2/1989 Howson et al. .................. 604/48

FOREIGN PATENT DOCUMENTS 1469132 12/1965 France ........................... 128/419 PS Primary Examiner—Lee S. Cohen
Assistant Examiner—Scott Getzow
Attorney, Agent, or Firm—Salter & Michaelson

[57] ABSTRACT

An electrical access port assembly includes an access port unit which is surgically implantable in the body of a patient and a pair of conductive needles which are operative for supplying electrical energy to the access port unit. The access port unit includes a body portion having a pair of access openings therein, a pair of penetrable elastomeric septa in the access openings, and an interior partition which divides the interior of the body portion into a pair of enclosed interior cavities, each of which is accessible through one of the penetrable septa. The access port unit further icludes an electrical contact in each of the cavities and a conductor wire attached to each of the contacts. The septa of the access port unit are self-sealingly penetrable by the conductive needles to electrically connect the needles to the contacts in the cavities in order to supply electrical energy to a predetermined location in the body of the patient through the conductor wires.

6 Claims, 2 Drawing Sheets

ELECTRICAL ACCESS PORT ASSEMBLY

BACKGROUND AND SUMMARY OF THE INVENTION

The instant invention relates to medical devices and more particularly to a surgically implantable electrical access port for conducting electrical energy to a predetermined location in the body of a patient.

A number of surgically implantable electrically powered medical devices have been developed over the course of the last few decades. The most common of these devices is the battery-powered heart pacer which is surgically implantable in the body of a patient so that it is operative for stimulating the heart muscle to operate with a regular repetitive beating pattern. It has been found that heart pacers only require a few microwatts of electrical energy to operate and hence they are generally capable of operating for periods of up to two years or more without replacing the batteries thereof. Nevertheless, it has been found that it is generally necessary to periodically surgically replace the batteries of devices of this type throughout the lives of patients in which they are installed. In addition to heart pacers, a number of other electrically powered devices have been developed for treating various medical conditions. However, many of these devices have been found to require several watts of electrical power to operate and hence they have required relatively large batteries which cannot practically be surgically implanted in patients. Accordingly, the only alternative has been to power devices of this type through external power sources, but since this practice severely limits the mobility of patients, it has normally only been used in extreme cases.

The instant invention provides an effective electrical access port assembly which is operative for supplying electrical energy to a predetermined location in the body of a patient in order to recharge an electrical storage battery and/or to power an electrically operated medical device implanted in the patient. Specifically, in its preferred form, the access port assembly of the instant invention comprises a surgically implantable body portion having first and second enclosed electrically insulated cavities therein, the body portion including first and second septa which are self-sealingly penetrable for gaining access to the first and second cavities, respectively, first and second electrical contacts in the first and second cavities, respectively, and first and second surgically implantable, insulated electrical conductors electrically connected to the first and second contacts, respectively. The access port assembly further comprises first and second electrically conductive needles, each including an elongated electrically insulated shank portion and an electrically exposed tip portion. The septa are adapted so that they are self-sealingly penetrable by the first and second needles for electrically connecting the tip portions of the needles to the first and second contacts, respectively, in a manner wherein the tip portions are located entirely within their respective cavities, and hence electrically insulated from the area surrounding the body portion. The access port assembly preferably further comprises an electrically insulated partition in the interior of the body portion which is substantially impenetrable by the needles and separates the first and second cavities. Each of the electrical contacts preferably comprises a contact brush including a plurality of closely spaced, substantially parallel, resilient, electrically conductive brush elements which are aligned so that the tip portion of a needle is receivable in engagement between a portion of the brush elements when the needle is inserted into the appropriate cavity in the body portion.

It has been found that the access port assembly of the instant invention can be utilized for effectively conducting electrical energy to a predetermined location in the body of a patient for either recharging a surgically implanted battery or for powering an implanted electrically powered medical device. Specifically, once the body portion and the conductor wires have been surgically implanted in a patient so that the body portion is located beneath the skin of the patient and the conductor wires extend to a predetermined location in the patient's body, the electrically conductive needles can be inserted through the skin of the patient so that they pass into the cavities through the septa in order to electrically connect the tip portions of the needles to the contacts in the cavities. Thereafter, by connecting the needles to an electrical power source, electrical energy can be supplied to the contacts in the body portion through the needles and then passed through the conductor wires to the predetermined location in the patient's body. As a result, it is possible to periodically recharge an electrical storage battery implanted in the body of a patient by periodically supplying electrical energy thereto through the access port so that the battery can remain in the body of the patient for an extended period of time without replacement. Further, it is practical to surgically implant a medical device which requires a relatively large amount of electrical energy in the body of a patient since the battery of the device can be recharged at regular intervals without invasive surgery. Still further, it is possible to periodically directly supply electrical power to an electrical device surgically implanted in the body of a patient without invasive surgical procedures.

Accordingly, it is a primary object of the instant invention to provide an access port assembly for supplying electrical energy to a predetermined location in the body of a patient.

Another object of the instant invention is to provide a means for recharging an electrical storage battery surgically implanted in the body of a patient.

An even further object of the instant invention is to provide an access port assembly comprising a surgically implantable body portion having a penetrable septum therein, an electrical contact in the body portion, a surgically implantable insulated electrical conductor wire connected to the electrical contact and an electrically conductive needle having an insulated shank portion and an uninsulated tip portion wherein the tip portion is electrically connectable to the contact in the body portion to supply electrical energy to the conductor wire.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Figure 1:
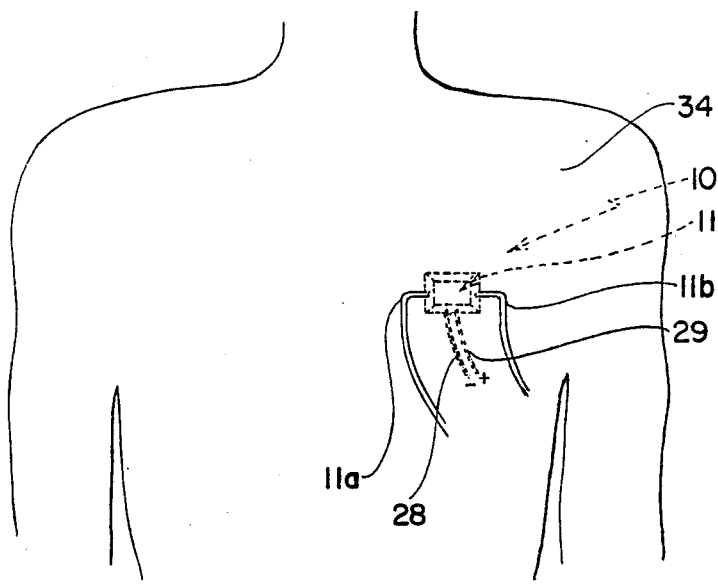
FIG. 1 is a schematic view illustrating the access port assembly of the instant invention installed in a patient.
Figure 2:
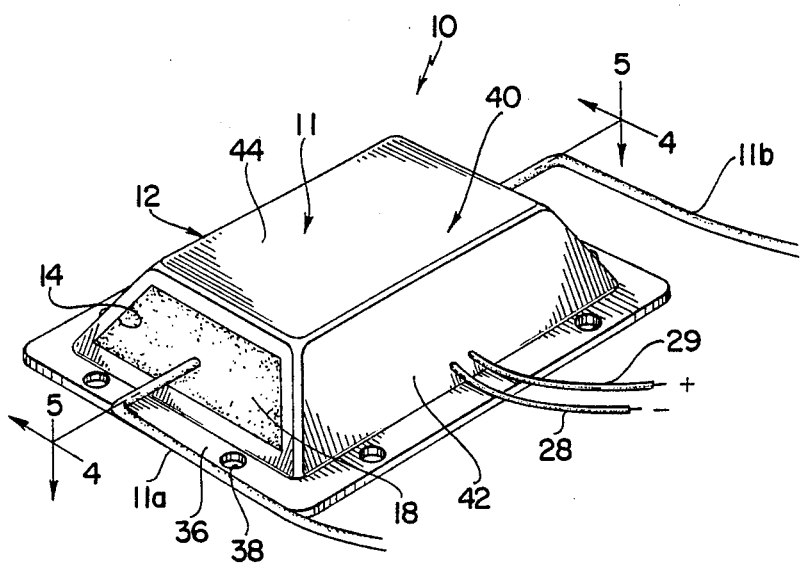
FIG. 2 is an enlarged perspective view of the access port assembly.
Figure 3:
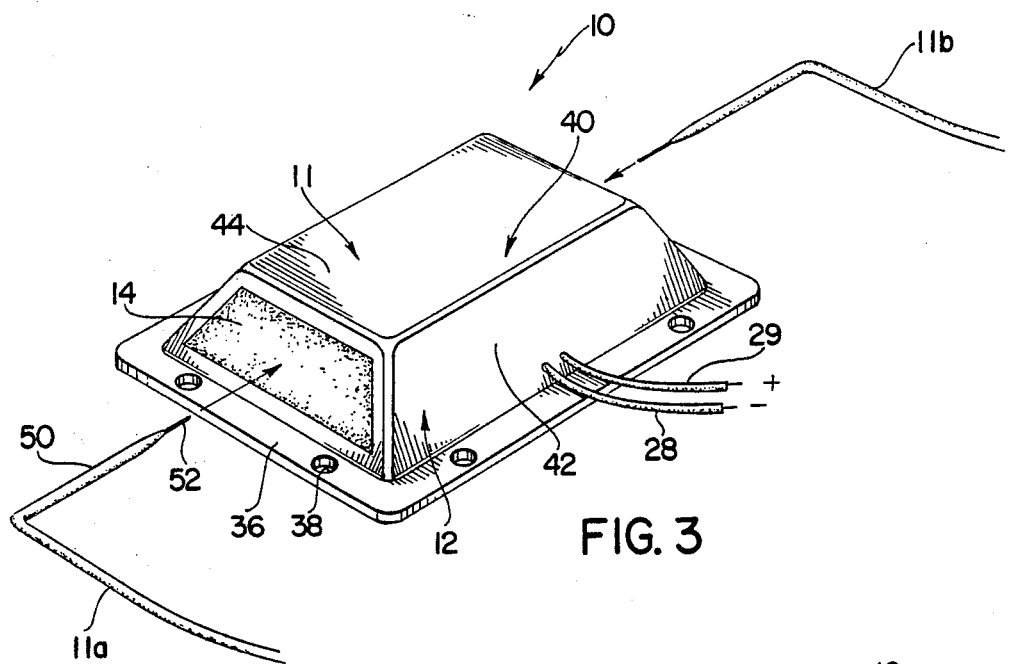
FIG. 3 is a similar view prior to passing the needles into the septum.

Referring now to the drawings, the access port assembly of the instant invention is illustrated and generally indicated at 10 in FIGS. 1-5. The access port assembly 10 comprises an implantable access port unit generally indicated at 11 and first and second needle elements generally indicated at 11a and 11b, respectively. The access port unit 11 comprises a body portion generally indicated at 12 having first and second access openings 14 and 16, respectively, therein, and first and second septa 18 and 20, respectively, received in the access openings 14 and 16, respectively, so that they cooperate with the remainder of the body portion 12 for defining first and second enclosed interior cavities 22 and 24, respectively. The access port unit 11 further comprises first and second contact assemblies generally indicated at 26 and 27, respectively, in the cavities 22 and 24, respectively, and first and second conductor wire elements 28 and 29, respectively, which are electrically connected to the first and second contact assemblies 26 and 27, respectively. As illustrated in FIG. 1, the access port unit 11 is adapted to be subcutaneously implanted in the body of a patient 34 so that it is penetrable by the needles 11a and 11b for supplying electrical energy to a predetermined location in the body of the patient 34.

The body portion 12 includes a base 36 having a plurality of suture apertures 38 therein and a wall portion generally indicated at 40 on the base 36. The wall portion 40 is of generally rectangular configuration and it includes a sidewall portion 42 which extends upwardly and slightly inwardly from the base 36 and a top wall portion 44. It will be understood, however, that a variety of other configurations for the wall portion are contemplated. The access openings 14 and 16 are formed at opposite ends of the sidewall portion 42, although other embodiments of the access port assembly of the instant invention which include the access openings which are formed in other locations, such as in the top wall portion 44, are contemplated. A partition 46 which is preferably made from a suitable nonelectrically conductive, non-toxic plastic material and constructed so that it is effectively impenetrable by the needle elements 11a and 11b extends upwardly from the base 36 to the top wall portion 44 for dividing the interior of the body portion 12 into the first and second cavities 22 and 24, respectively. Again, however, it will be understood that other embodiments of the access port of the instant invention wherein the partition 46 is positioned in other locations in the interior of the body portion 12 are contemplated.

The septa 18 and 20 are made from a suitable electrical insulating elastomeric material, such as a silicone rubber so that they are self-sealingly penetrable by the needles 11a and 11b, respectively, and self-sealing upon removal of the needles therefrom. The septa 18 and 20 are received in the access openings 14 and 16, respectively and accordingly, they cooperate with the body portion 12 to define the enclosed interior cavities 22 and 24, respectively, and because the septa 18 and 20 and the remainder of the body portion 12 are made from electrical insulating materials, the cavities 22 and 24 are electrically insulated from the exterior areas surrounding the access port unit 11.

Figure 4:
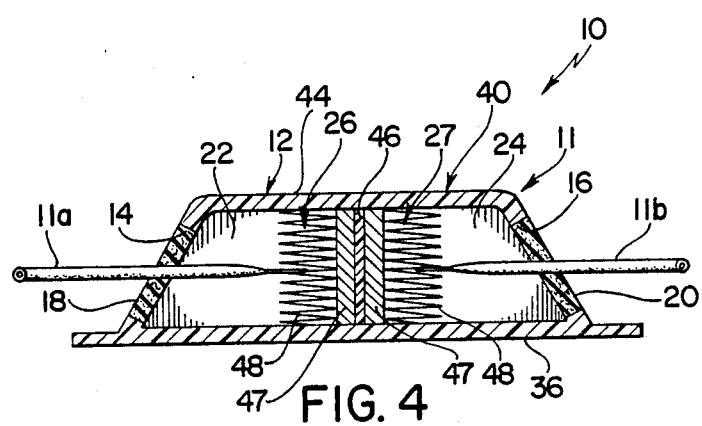
FIG. 4 is a sectional view taken along line 4—4 in FIG. 2.
Figure 5:
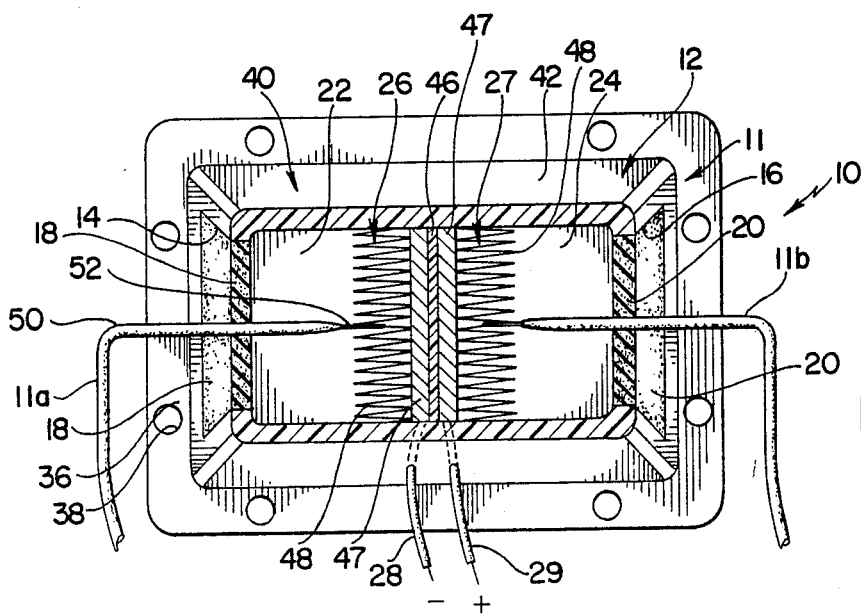
FIG. 5 is a sectional view taken along line 5—5 in FIG. 2.

Each of the contact assemblies 26 and 27 comprises a contact brush including an electrically conductive plate-like base portion 47 having a plurality of outwardly extending wire brush elements 48 thereon. The base portions 47 of the contact assemblies 26 and 27 are mounted on opposite sides of the partition 46 in the cavities 22 and 24, respectively, so that the wire brush elements 48 thereof project toward the septa 18 and 20, respectively, as illustrated in FIGS. 4 and 5. The wire brush elements 48 are preferably disposed in closely spaced substantially parallel relation and they are made from a suitable conductive metal. Accordingly, the wire brush elements 48 of the contact assemblies 26 and 27 are adapted to receive the tip portions of the needle elements 11a and 11b therebetween for supplying electrical energy to the contact assemblies 26 and 27 as will hereinafter be more fully set forth. In this regard, it will be understood, however, that the use of various other types of contact assemblies, such as conductive liquids, slurries, springs, beads, powders, etc. in the cavities 22 and 24 is contemplated.

The conductor wires, 28 and 29 are electrically connected to the base portions 47 of the contact assemblies 26 and 27, respectively. The conductors 28 and 29 comprise insulated electrical conductors which are made from suitable non-toxic materials to enable them to be effectively surgically implanted in the body of a patient for conducting electrical energy to a predetermined location therein.

The needle elements 11a and 11b are adapted for penetrating through the septa 18 and 20, respectively, and they are adapted to be electrically connected to the contact assemblies 26 and 27, respectively, in the manner illustrated in FIGS. 4 and 5. The needle elements 11a and 11b are made from a suitable non-toxic material and they are adapted to be utilized for penetrating the skin of the patient 34 before they penetrate the septa 18 and 20, respectively. The needle elements 11a and 11b include insulated shank portions 50 and uninsulated or electrically exposed tip portions 52. The shank portions 50 are preferably formed in right angle configurations and they include conductive core wires which are electrically connected to the tip portions 52 thereof. The shank portions 50 and the tip portions 52 are dimensioned to enable the needle elements 11a and 11b to penetrate the septa 18 and 20 so that the respective tip portions 52 thereof are in electrical contact with the contact assemblies 26 and 27, respectivley, and disposed entirely in their respective cavities 22 or 24. The septa 18 and 20 are adapted to self-sealingly engage the insulated shank portions 50 of the needles 11a and 11b so that when the respective tip portions 52 thereof are in electrical contact with their contact assemblies 26 and 27, the tip portions 52 are electrically isolated from the areas surrounding the exterior of the access port unit 11. The tip portions 52 are further dimensioned so that they can pass between the wire brush elements 48 in the contact assemblies 26 and 27 in order to electrically connect the tip portions 52 to their respective contact assemblies 26 or 27.

For use and operation of the access port assembly 10, the access port unit 11 is implanted in the body of a patient so that the body portion 12 is positioned beneath the patient's skin and so that the conductor wires, 28 and 29 extend to a predetermined location in the patient's body, such as the location of an implanted electrical storage battery. Once the port unit 11 has been installed in a patient in this manner, the needle elements 11a and 11b can be utilized for electrically connecting the port unit 11 to an external electrical power source. Specifically, by inserting the tip portions 52 and the adjacent shank portions 50 of the needle elements 11a and 11b through the skin of the patient so that the tip portion 52 of the needle element 11a passes through the septum 18 and the tip portion 52 of the needle element 11b passes through the septum 20, the tip portions 52 can be electrically connected to the wire brush elements 48 in order to electrically connect the needle elements 11a and 11b to the conductor wires 28 and 29, respectively. In this regard, when the needle elements 11a and 11b have penetrated the septa 18 and 20, respectively, so that the tip portions 52 of the needle elements 11a and 11b are located entirely within the cavities 22 and 24, respectively, the septa 18 and 20 sealingly engage the shank portions 50 of the needle elements 11a and 11b, respectively to electrically isolate the tip portions 52 thereof from the exterior of the access port unit 11. Accordingly, by energizing the needle elements 11a and 11b with an appropriate power source, electrical current can be supplied to the conductor wires 28 and 29 for supplying electrical power to a device, such as a storage battery or a previously implanted electrically powered medical device. Further, once a sufficient amount of electrical energy has been supplied to the storage battery or medical device through the wires 28 and 29, the flow of current through the needle elements 11a and 11b can be discontinued, and the needle elements 11a and 11b can be removed from the patient.

It is seen therefore that the instant invention provides an effective electrical access port assembly for supplying electrical energy to a predetermined location in the body of a patient. The access port assembly 10 is adapted so that the needle elements 11a and 11b can be inserted into the access port unit 11 to supply electrical energy to a predetermined location in the body of a patient through the conductor wires 28 and 29. Accordingly, the access port assembly 10 can be effectively utilized for recharging an electrical storage battery in the body of the patient and/or for energizing various electrically powered medical devices in the patient. Accordingly, for these reasons as well as the other reasons hereinabove set forth, it is seen that the access port assembly of the instant invention represents a significant advancement which has substantial merit in the medical art.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. An electrical access port assembly for supplying electrical energy to a predetermined location in the body of a patient comprising a surgically implantable body portion having first and second enclosed, electrically insulated interior cavities therein, said body portion including first and second penetrable septa which are self-sealingly penetrable to gain access to said first and second cavities, respectively, first and second electrical contact means in said first and second cavities, respectively, first and second insulated electrical conductor means electrically communicating with said first and second electrical contact means, respectively, said conductor means being surgically implantable in the body of said patient so that they extend to said predetermined location therein, and first and second electrically conductive needle means, each including an elongated electrically insulated shank portion and an electrically exposed tip portion, said first and second septa being self-sealingly penetrable by said first and second needle means, respectively, for electrically connecting the tip portions of said first and second needle means to said first and second contact means, respectively, without otherwise electrically connecting said first and second needle means to the body of said patient when said access port is surgically implanted in said patient.

2. The access port assembly of claim 6 further comprising an interior partition in said body portion, said partition separating said first and second cavities and being substantially impenetrable by said first and second needle means.

3. In the access port assembly of claim 1, said body portion comprising a wall portion, said first and second septa being located in said wall portion.

4. In the access port assembly of claim 1, said body portion comprising a sidewall portion, said first and second septa being located in said sidewall portion.

5. In the access port assembly of claim 4, said septa being made of an elastomeric material.

6. A surgically implantable electrical access port comprising a surgically implantable body portion having first and second enclosed, electrically insulated interior cavities therein, said body portion including first and second self-sealingly penetrable septa, first and second electrical contact means in said first and second cavities, respectively, and first and second insulated electrical conductor means electrically connected to said first and second contact means, respectively, said first and second conductor means being surgically implantable in the body of a patient so that they extend to a predetermined location therein for effecting electrical communication between said first and second contact means and said predetermined location.

* * * * *